US009818005B2

(12) United States Patent
Yeager et al.

(10) Patent No.: US 9,818,005 B2
(45) Date of Patent: Nov. 14, 2017

(54) ZERO-POWER WIRELESS DEVICE PROGRAMMING

(71) Applicant: Verily Life Sciences LLC, Mountain View, CA (US)

(72) Inventors: Daniel James Yeager, Mountain View, CA (US); Brian Otis, Mountain View, CA (US); Nathan Pletcher, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 299 days.

(21) Appl. No.: 14/303,674

(22) Filed: Jun. 13, 2014

(65) Prior Publication Data
US 2015/0363614 A1  Dec. 17, 2015

(51) Int. Cl.
*H04W 4/00* (2009.01)
*G06K 7/10* (2006.01)
(Continued)

(52) U.S. Cl.
CPC ....... *G06K 7/10158* (2013.01); *G06K 19/073* (2013.01); *H04W 4/003* (2013.01); *A61B 2562/08* (2013.01); *G06K 19/0716* (2013.01)

(58) Field of Classification Search
CPC ............ G06K 19/0712; G06K 19/0723; H04L 63/0428; H04L 2209/805; H04L 9/0822; H04W 4/003
See application file for complete search history.

(56) References Cited

U.S. PATENT DOCUMENTS

| 4,856,062 A | * | 8/1989 | Weiss | ...................... | G06F 21/34 |
| | | | | | 713/184 |
| 6,288,629 B1 | * | 9/2001 | Cofino | ................. | G06K 7/0008 |
| | | | | | 340/10.1 |

(Continued)

FOREIGN PATENT DOCUMENTS

| WO | 2009099498 A1 | 8/2009 |
| WO | 2012112703 A1 | 8/2012 |

(Continued)

OTHER PUBLICATIONS

International Search Report and Written Opinion for PCT/US2015/035618 dated Sep. 22, 2015.
(Continued)

*Primary Examiner* — Steven Lim
*Assistant Examiner* — Kam Ma
(74) *Attorney, Agent, or Firm* — McDonnell Boehnen Hulbert & Berghoff LLP

(57) ABSTRACT

The present disclosure provides methods and apparatuses for loading program data on to an unpowered electronic device, such as an RFID tag that includes volatile memory. Initially, the tag is unpowered. Thus, the volatile memory in the tag will not have any stored data. In order to load data into the memory of the tag, a reader can power the tag wirelessly. The reader includes an antenna configured to transmit electromagnetic radiation and receive backscatter electromagnetic radiation. The reader also includes a processing unit. The processing unit is configured to analyze the backscatter electromagnetic radiation. The processing unit may analyze the backscatter radiation to determine a supply voltage induced in the tag. In response to the induced voltage being greater than a threshold, the processing unit may alter the transmitted electromagnetic radiation to communicate tag data.

18 Claims, 7 Drawing Sheets

(51) Int. Cl.
*G06K 19/073* (2006.01)
*G06K 19/07* (2006.01)

(56) References Cited

U.S. PATENT DOCUMENTS

| | | | | |
|---|---|---|---|---|
| 6,629,047 | B1* | 9/2003 | Guliani | G11C 16/225 |
| | | | | 702/108 |
| 6,868,073 | B1* | 3/2005 | Carrender | G01S 13/84 |
| | | | | 340/572.1 |
| 6,938,177 | B1 | 8/2005 | Blemel | |
| 7,120,550 | B2* | 10/2006 | Diorio | G06K 19/0726 |
| | | | | 702/107 |
| 7,274,304 | B2* | 9/2007 | Hall | E21B 47/12 |
| | | | | 340/853.3 |
| 7,579,955 | B2* | 8/2009 | Pillai | G06K 19/0723 |
| | | | | 340/10.4 |
| 7,733,227 | B1* | 6/2010 | Pesavento | G06K 7/0008 |
| | | | | 340/10.1 |
| 7,806,332 | B2* | 10/2010 | Satou | G06K 19/0701 |
| | | | | 235/435 |
| 7,817,040 | B2 | 10/2010 | Homanfar et al. | |
| 7,889,055 | B2* | 2/2011 | Akiyama | G06K 19/0723 |
| | | | | 340/10.1 |
| 8,098,159 | B2* | 1/2012 | Batra | G06K 19/0716 |
| | | | | 340/10.1 |
| 8,340,577 | B2* | 12/2012 | Griffin | H04B 5/0062 |
| | | | | 340/568.1 |
| 8,390,431 | B1 | 3/2013 | Diorio | |
| 8,427,296 | B2 | 4/2013 | Pance et al. | |
| 8,436,491 | B2 | 5/2013 | Walley | |
| 8,558,699 | B2 | 10/2013 | Butler | |
| 8,608,310 | B2 | 12/2013 | Otis et al. | |
| 8,636,358 | B2 | 1/2014 | Binder | |
| 8,688,140 | B2* | 4/2014 | Nemeth | G01S 1/302 |
| | | | | 370/329 |
| 8,941,469 | B1* | 1/2015 | Diorio | H04L 9/3247 |
| | | | | 340/10.1 |
| 9,244,162 | B2* | 1/2016 | Viikari | G01S 13/756 |
| 2004/0208064 | A1* | 10/2004 | Sohn | G11C 8/16 |
| | | | | 365/189.04 |
| 2005/0052279 | A1* | 3/2005 | Bridgelall | G06K 7/0008 |
| | | | | 340/10.1 |
| 2005/0070811 | A1* | 3/2005 | Crowley | G01K 1/024 |
| | | | | 600/549 |
| 2006/0007771 | A1* | 1/2006 | Sato | G11C 5/142 |
| | | | | 365/226 |
| 2006/0085655 | A1* | 4/2006 | Sung | G06K 19/0707 |
| | | | | 713/300 |
| 2006/0169769 | A1* | 8/2006 | Boyarsky | G06Q 20/18 |
| | | | | 235/381 |
| 2006/0175420 | A1* | 8/2006 | Satou | G06K 19/0701 |
| | | | | 235/492 |
| 2006/0176152 | A1* | 8/2006 | Wagner | G06K 7/0008 |
| | | | | 340/10.2 |
| 2006/0238302 | A1* | 10/2006 | Loving | G06K 7/0008 |
| | | | | 340/10.1 |
| 2007/0120651 | A1* | 5/2007 | Kobayashi | H04B 5/0056 |
| | | | | 340/10.51 |
| 2007/0285237 | A1* | 12/2007 | Batra | G06K 19/0716 |
| | | | | 340/572.1 |
| 2008/0093447 | A1 | 4/2008 | Johnson et al. | |
| 2009/0076367 | A1 | 3/2009 | Sit et al. | |
| 2009/0115638 | A1* | 5/2009 | Shankwitz | G01C 21/26 |
| | | | | 340/988 |
| 2009/0215408 | A1* | 8/2009 | Evers | G01S 13/758 |
| | | | | 455/90.1 |
| 2009/0315673 | A1* | 12/2009 | Huang | G06K 7/0008 |
| | | | | 340/5.61 |
| 2010/0039230 | A1* | 2/2010 | Voutilainen | G01R 31/2822 |
| | | | | 340/10.1 |
| 2010/0110372 | A1 | 5/2010 | Pugh et al. | |
| 2011/0055351 | A1* | 3/2011 | Boldyrev | H04B 5/0031 |
| | | | | 709/219 |
| 2012/0007441 | A1* | 1/2012 | John | A61N 1/3785 |
| | | | | 307/104 |
| 2012/0046069 | A1* | 2/2012 | Cupala | G06F 8/65 |
| | | | | 455/550.1 |
| 2012/0214462 | A1 | 8/2012 | Chu et al. | |
| 2012/0274449 | A1 | 11/2012 | Wilkinson | |
| 2013/0082536 | A1 | 4/2013 | Taylor | |
| 2013/0145199 | A1 | 6/2013 | Fu et al. | |
| 2013/0147609 | A1* | 6/2013 | Griffin | G06K 7/10158 |
| | | | | 340/10.5 |
| 2013/0194540 | A1 | 8/2013 | Pugh | |
| 2013/0271265 | A1 | 10/2013 | Finn | |
| 2014/0085083 | A1* | 3/2014 | Sabeta | G06K 19/07758 |
| | | | | 340/539.12 |
| 2014/0107444 | A1* | 4/2014 | Liu | A61B 5/0004 |
| | | | | 600/345 |
| 2014/0107445 | A1 | 4/2014 | Liu | |
| 2015/0032569 | A1* | 1/2015 | Stromberg | G06K 7/10009 |
| | | | | 705/26.35 |
| 2015/0363614 | A1* | 12/2015 | Yeager | G06K 7/10158 |
| | | | | 340/10.5 |

FOREIGN PATENT DOCUMENTS

| | | |
|---|---|---|
| WO | 2013069472 A2 | 5/2013 |
| WO | 2013089458 A1 | 6/2013 |

OTHER PUBLICATIONS

Search Report and Written Opinion for PCT/US2015/035618 dated Dec. 22, 2016.
Search Report and Written Opinion for PCT/US2015/030393 dated Dec. 22, 2016.

* cited by examiner

ZERO-POWER WIRELESS DEVICE PROGRAMMING

BACKGROUND

Unless otherwise indicated herein, the materials described in this section are not prior art to the claims in this application and are not admitted to be prior art by inclusion in this section.

Some electronic devices are of sufficiently small size that a power supply cannot reasonably accompany the device. In these instances, the electronic device may receive power from an external power source. The external power source may be configured to supply power to the electronic device wirelessly. Further, due to both its small size and power constraints the electronic device may be configured with a volatile memory. A volatile memory stores data only as long as a electricity is supplied to the memory. Thus, if a device runs out of power, the memory may revert to a blank state.

SUMMARY

One aspect of the present disclosure provides a reader apparatus. The reader apparatus includes an antenna. The antenna is configured to transmit electromagnetic radiation and receive backscatter electromagnetic radiation. The reader apparatus also includes a processing unit. The processing unit is configured to analyze the backscatter electromagnetic radiation. The processing unit may analyze the backscatter radiation to determine an induced voltage. In response to the induced voltage being greater than a threshold, the processing unit may alter the transmitted electromagnetic radiation to communicate tag data.

In yet another aspect, the present disclosure provides a body-mountable device. The body-mountable device includes an antenna. The antenna is an antenna configured to receive first electromagnetic radiation during a first period of time, and receive second electromagnetic radiation during a second period of time. The received second electromagnetic radiation may be configured to communicate data. The body-mountable device may also be configured to output a first signal with the antenna based on the received first electromagnetic radiation. Additionally, the body-mountable device includes a rectification circuit configured to rectify at least the first signal to generate a supply voltage. The body-mountable device is also further configured with a volatile memory. The volatile memory is configured to be powered by the supply voltage and configured to store the data communicated via the second electromagnetic radiation.

Another aspect of the present disclosure provides a method. The method includes transmitting electromagnetic radiation via an antenna. The method also includes receiving backscatter electromagnetic radiation via the antenna and analyzing the backscatter electromagnetic radiation to determine an induced voltage. Further, the method includes in response to the induced voltage being greater than a threshold, altering the transmitted electromagnetic radiation to communicate tag data.

These as well as other aspects, advantages, and alternatives, will become apparent to those of ordinary skill in the art by reading the following detailed description, with reference where appropriate to the accompanying drawings.

DETAILED DESCRIPTION

Figure 1:
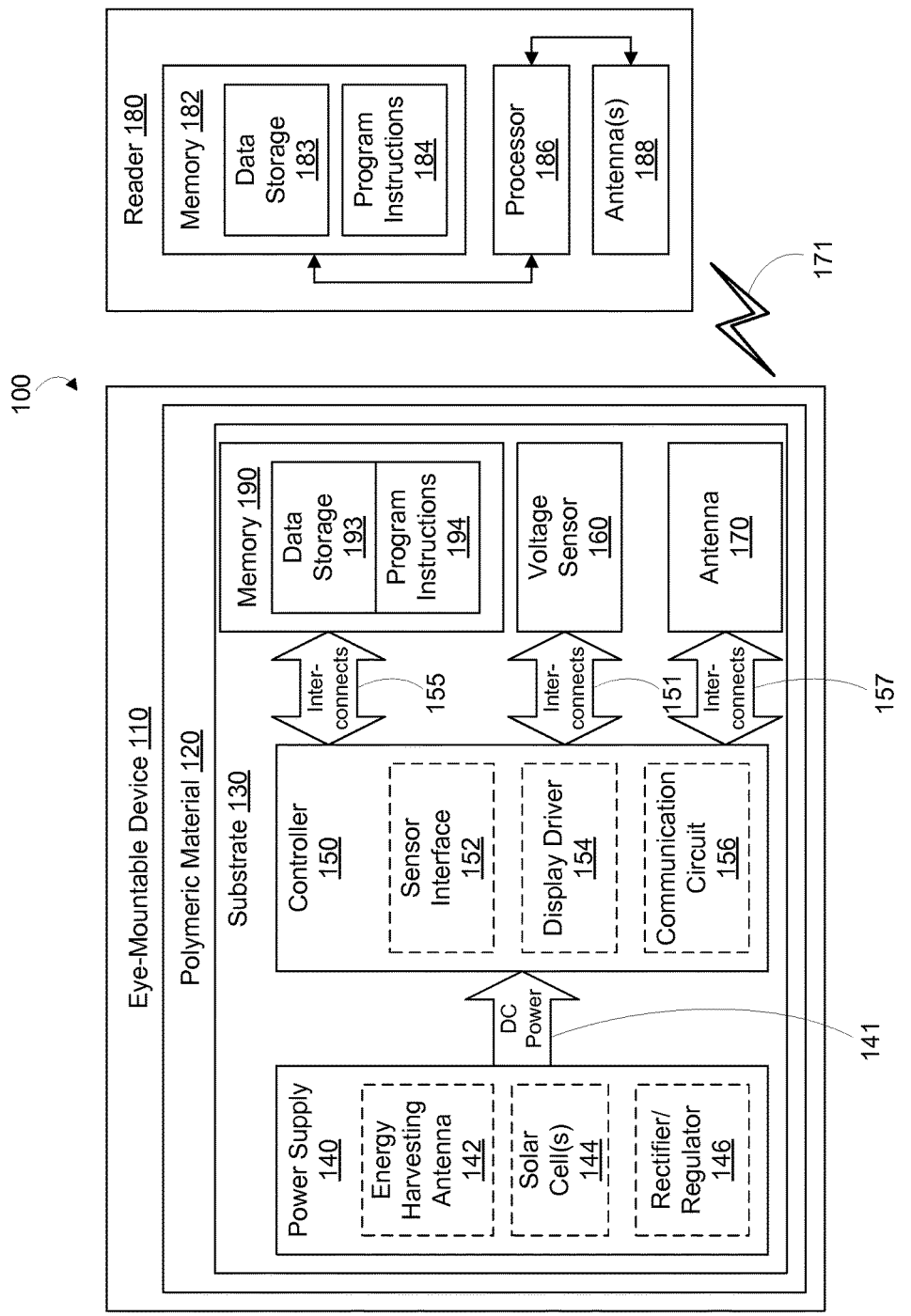
FIG. 1 is a block diagram of an example system that includes an eye-mountable device in wireless communication with a reader, in accordance with an example embodiment.

One aspect of the present disclosure provides a method for loading program data on to an unpowered electronic device, such as an RFID tag that includes volatile memory. After a tag is manufactured and shipped, the tag will be unpowered. Thus, the volatile memory in the tag will not be powered. In order to load data into the volatile memory of the tag, the tag can be provided with sufficient power for the memory to operate. In an example embodiment, an external reader device or "reader" can radiate radio frequency radiation to power the tag. The reader may thereby control the operation of the tag by controlling the supply of power to the tag. In some examples, the reader can operate to intermittently interrogate the tag to provide a reading by radiating sufficient radiation to power the tag to obtain a measurement and communicate the result.

An external reader may be used to transmit power to the tag with a radio frequency signal or Extremely low frequency (ELF) signal, such as an electromagnetic field or a magnetic field. The tag may rectify the radio frequency electromagnetic signal and create a rectified voltage. This rectified voltage may be used to power various components of the tag, such as the volatile memory, and also charge a power supply (e.g., a battery or capacitor) within the tag.

In some embodiments, the tag may be located on a contact lens. The reader may take the form of a handheld device, such as a mobile phone, tablet computer, or dedicated reader. To read and communicate power to the tag, the reader is placed within a relatively close proximity to the tag. In one example, the reader may be moved near an eye on which a contact lens having a tag is mounted.

Once it transmits power to the tag, the reader may communicate data to the tag. The data may take the form of program instructions. A processing unit coupled to the tag may execute the program instructions. In some embodiments, the processor can be integrated into a first integrated circuit (IC) that performs the rectification and communication. In other embodiments, the processor can be a second IC inside the lens/packaging that is connected to the first IC. When executed, the program instructions may cause components associated with the tag to perform various functions. Functions may include sampling from sensors connected to the tag (e.g. sampling a glucose level), creating a visual output with an output device (e.g. one or more LEDs) based on various parameters of the tag (e.g. battery level, glucose level, memory space remaining).

The external reader may also include processing logic. The external reader receives a backscatter signal from the tag. The backscatter radiation may contain data relating to an indication of a voltage from the tag and compare the voltage to the voltage required for certain functionality of the tag. In some embodiments, the tag may contain various electrical components, such as sensors and memory. For example, some functionality of the tag device may run on 0.7 Volt while other functionality may require 1 Volt for correct operation. Therefore, before a memory can be written to, the voltage of the tag may need to be greater than to equal to a memory voltage threshold.

The tag can be configured with, or be part of, a Radio-frequency Identification (RFID) protocol communication link. The RFID tag and reader can communicate using an RFID protocol; e.g., an RFID Generation 2 protocol. The RFID tag can be configured to receive radio signals from the reader. In some embodiments, the reader's signals can be used for both communicating with and powering the RFID tag. In other embodiments, the RFID tag can be a powered device; e.g., be configured with a battery that powers the tag. In embodiments in which a battery powers the tag, the reader's signals may be used to charge the battery. Therefore, the battery may be wirelessly charged and data may be written to the tag in situ.

The reader can communicate with other devices than the RFID tag. As one possible example, the reader can be equipped with a Bluetooth interface as well as with an RFID interface. The reader can communicate with other devices, e.g., a display device, via a Bluetooth or other protocol. In one example, the reader can obtain data from the RFID tag using RFID command(s); e.g., the RFID Generation 2 standard Read command. Upon obtaining the data, the reader can store, process, and/or communicate the data using the Bluetooth interface to another device, such as the display device. Other interfaces for communicating with devices using other communication protocol(s) are possible as well.

Additionally, functions may include a data-compression algorithm that enables the tag to compress data before it communicates the data back to the reader. In some embodiments, the tag may also include a small amount of non-volatile memory. The non-volatile memory may be configured to store a cryptographic key and/or identification information, configuration/calibration data. The cryptographic key may be used to verify that data written to the tag is from a verified source. The non-volatile memory may be configured to be written to once. Thus, when a cryptographic key is stored it cannot be changed. In some further embodiments, a custom set of RFID commands may be used with a tag when the tag has a cryptographic key.

In some embodiments, the tag may be able to measure the level of a rectified voltage that the reader induced in the tag. The tag may communicate the rectified voltage level back to the reader. Once the reader determines the voltage in the tag is high enough to power the volatile memory, the reader may communicate data to write to the volatile memory of the tag.

As an example, the above-mentioned contact lens system can be configured with a sensor that includes an RFID tag. As mentioned above, the sensor can be configured to take measurements while being worn in an eye of a wearer. Upon taking the measurements, the sensor may store data related to the measurements, and subsequently send the data upon request from the reader. The reader, in turn, can store and/or process the received data. For example, the sensor can take measurements of a supply voltage in the tag. The reader can process the supply voltage data to determine if the supply voltage is large enough to power various components of the tag, such as a sensor or a memory. The determination may be based on a desired functionality of the tag.

This disclosure will generally describe the tag as being located in a contact lens; however, the disclosed methods and apparatuses do not require the tag be part of a contact lens. In additional embodiments, the tag may be located on various items, such as a watch, a wristband, an earring, or other body-worn location. In various embodiments, the tag may be programmed with data in response to the tag having a voltage greater than a memory voltage threshold.

In some embodiments, the reader can be configured to be worn in proximity to one or more eye-mountable devices that include sensors. For example, the reader can be configured to be part of a pair of eyeglasses, jewelry (e.g., earrings, necklace), headband, head cover such as a hat or cap, earpiece, other clothing (e.g., a scarf), HMD, and/or other devices. As such, the reader can provide power and/or receive measurements while proximate to the worn contact lens(es).

In other embodiments, both the display and the reader may be combined into a single unit. For example, a device, such as a mobile phone, may have functionality to act as both the display and the reader to interact with the tag.

Configuring the reader to be frequently worn in proximity to one or more eye-mountable devices enables the devices to have a reliable external power source and/or storage for sensor data collection, processing of sensor data, and transmission of unprocessed and/or processed sensor data to additional devices; e.g., the above-mentioned display device. Thus, the herein-described reader can provide valuable support functionality, including but not limited to power, communication, and processing resources.

FIG. 1 is a block diagram of a system 100 that includes an eye-mountable device 110 in wireless communication with a reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, voltage sensor 160, and a communication antenna 170. The voltage sensor 160 may be operated by the controller 150 or it may operate based on receiving the DC Power 141. The power supply 140 supplies operating voltages to the controller 150 and/or the voltage sensor 160. The antenna 170 is operated by the controller 150 to communicate information to and/or from the eye-mountable device 110. The antenna 170, the controller 150, the power supply 140, and the voltage sensor 160 can all be situated on the embedded substrate 130. Because the eye-mountable device 110 includes electronics and is configured to be contact-mounted to an eye, it may also be referred to as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the voltage sensor 160, the controller 150, the power supply 140, memory 190, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the voltage sensor 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a voltage sensor 160 can be mounted to one substrate, while the antenna 170 is mounted to another substrate and the two can be electrically connected via the interconnects 157.

In some embodiments, the voltage sensor 160 (and the substrate 130) can be positioned away from the center of the eye-mountable device 110 and thereby avoid interference with vision. For example, where the eye-mountable device 110 is shaped as a concave-curved disk, the substrate 130 can be embedded around the periphery (e.g., near the outer circumference) of the disk. In some embodiments, however, the voltage sensor 160 (and the substrate 130) can be positioned in or near the central region of the eye-mountable device 110. Additionally or alternatively, the voltage sensor 160 and/or substrate 130 can be substantially transparent to incoming visible light to mitigate interference with light transmission to the eye. Moreover, in some embodiments, the voltage sensor 160 can include a pixel array (not shown) that emits and/or transmits light to be received by the eye according to display instructions. Thus, the voltage sensor 160 can optionally be positioned in the center of the eye-mountable device so as to generate perceivable visual cues to a wearer of the eye-mountable device 110, such as by displaying information (e.g., characters, symbols, flashing patterns, etc.) on the pixel array.

The substrate 130 can be ring-shaped with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and voltage sensor 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the voltage sensor 160 and the antenna 170. The controller 150 can include logic circuitry configured to operate the voltage sensor 160 so as to interact with the antenna 170 to control the impedance of the antenna 170. The impedance of the antenna 170 may be used to communicate via backscatter radiation. Antenna 170 and backscatter radiation are discussed further below.

The controller 150 can also include logic circuitry configured to read and write to memory 190. Additionally, the controller 150 may execute program instructions stored in memory 190. Further, memory 190 may contain both volatile and non-volatile memory components. The memory 190 can include a data storage 193 to store indications of data, such as sensor readings (e.g., from the voltage sensor 160), program settings (e.g., to adjust behavior of the eye-mountable device 110), etc. The memory 190 can also include program instructions 194 for execution by the controller 150 to perform processes specified by the instructions 194. For example, the program instructions 194 can cause the controller 150 to operate the sensor interface 152. Additionally, the controller 150 may receive program instructions communicated from the reader 180 and store the program instructions in the program instruction 194 of the memory 190.

In one example, the controller 150 includes a sensor interface module 152 that is configured to interface with the voltage sensor 160. The voltage sensor 160 can be, for example, an electrical sensor configured to provide an output based on an input voltage of the voltage sensor 160. A voltage can be applied at the input of the voltage sensor 160. The voltage sensor 160 may responsively create an output based on the input voltage. However, in some instances the input voltage may not be sufficiently high to power the voltage sensor 160. When the input voltage is not high enough to power the voltage sensor 160, the voltage sensor 160 may not provide any output. Although the current disclosure generally referrers to voltage sensor 160 as sensing a voltage, various other electrical sensors may be used in the place of voltage sensor 160. For example, a current sensor, a power sensor, or other electrical sensor may be used in the place of the voltage sensor 160 within the context of the present disclosure.

The controller 150 can optionally include a display driver module 154 for operating a pixel array. The pixel array can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array can also optionally include more than one color of pixels (e.g., red, green, and blue pixels) to render visual content in color. The display driver module 154 can include, for example, one or more data lines providing programming information to the separately programmed pixels in the pixel array and one or more addressing lines for setting groups of pixels to receive such programming information. Such a pixel array situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. As previously stated, in some examples, the eye-mountable device 110 is configured to indicate an output from a voltage sensor 160 by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the voltage sensor 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the voltage sensor 160. Similarly, the controller 150 is connected to the antenna 170 via interconnects 157. Further, the controller 150 is connected to the memory 190 via interconnects 155.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can be configured to be external to the eye; i.e., is not part of the eye-mountable device. Reader 180 can include one or more antennas 188 to send and receive wireless signals 171 to and from the eye-mountable device 110. In some embodiments, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the voltage sensor 160), program settings (e.g., to adjust behavior of the eye-mountable device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the eye-mountable device 110 (e.g., sensor outputs from the voltage sensor 160). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

In some embodiments, reader 180 can be a smart phone, digital assistant, or other portable computing device with wireless connectivity sufficient to provide the wireless communication link 171. In other embodiments, reader 180 can be implemented as an antenna module that can be plugged in to a portable computing device; e.g., in scenarios where the communication link 171 operates at carrier frequencies not commonly employed in portable computing devices. In even other embodiments discussed below in more detail, the reader 180 can be a special-purpose device configured to be worn relatively near a wearer's eye to allow the wireless communication link 171 to operate with a low power budget. For example, the reader 180 can be integrated in eye glasses, in a piece of jewelry such as a necklace, earring, etc. or integrated in an article of clothing worn near the head, such as a hat, headband, etc. Further, the reader 180 may have a display element that is within view of an eye of the wearer.

Figure 2A:
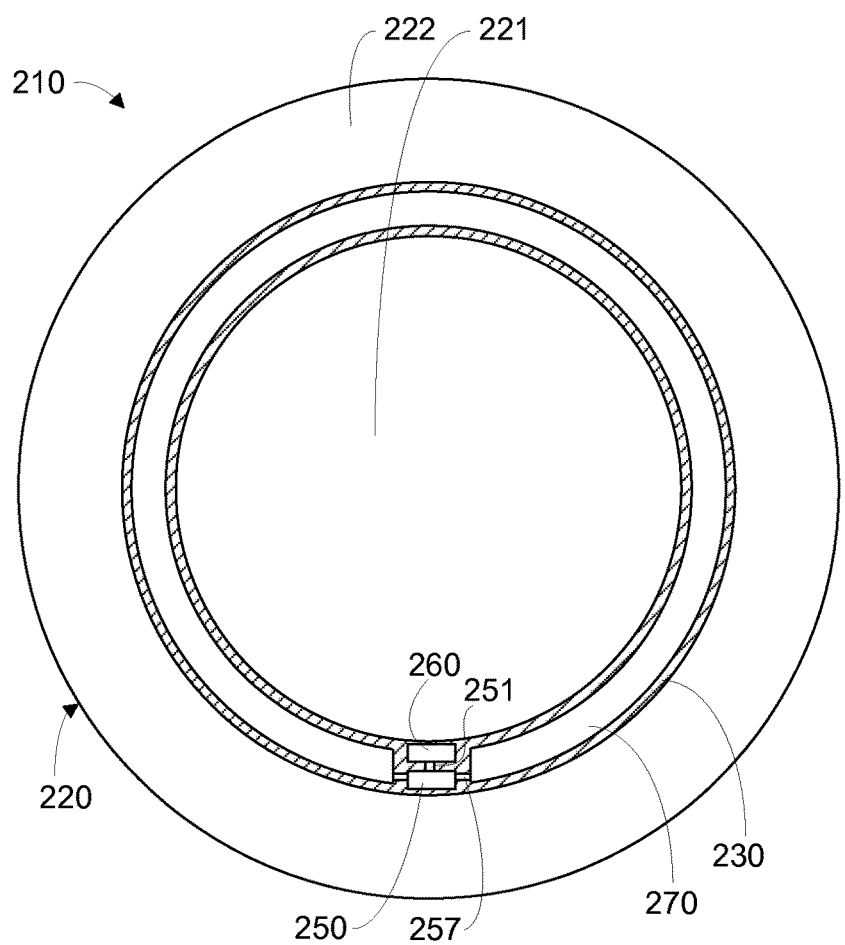
FIG. 2A is a top view of an example eye-mountable device, in accordance with an example embodiment.
Figure 2B:
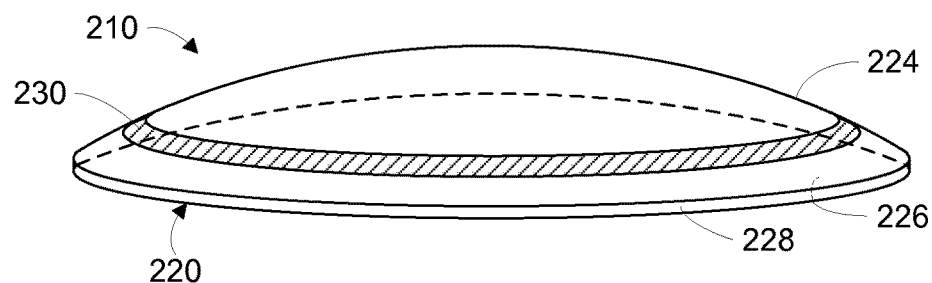
FIG. 2B is a side view of the example eye-mountable device shown in FIG. 2A, in accordance with an example embodiment.

FIG. 2A is a top view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device (EMD) 210. The EMD 210 is formed of a polymeric material 220 shaped as a curved disk. In some embodiments, EMD 210 can include some or all of the above-mentioned aspects of eye-mountable device 110. In other embodiments, eye-mountable device 110 can further include some or all of the herein-mentioned aspects of EMD 210.

The polymeric material 220 can be a substantially transparent material to allow incident light to be transmitted to the eye while the EMD 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the EMD 210 is mounted to the eye. A circular outer side edge 228 connects the concave surface 224 and convex surface 226.

The EMD 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the EMD 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the EMD 210 is mounted in an eye, the convex surface 224 faces outward to the ambient environment while the concave surface 226 faces inward, toward the corneal surface. The convex surface 224 can therefore be considered an outer, top surface of the EMD 210 whereas the concave surface 226 can be considered an inner, bottom surface. From the top view shown in FIG. 2A, the outer periphery 222, near the outer circumference of the curved disk is curved to extend in to the page, whereas the central region 221, near the center of the disk is curved to extend out of the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and voltage sensor 260 are disposed on the embedded substrate 230. The controller 250 can be a chip including logic elements configured to operate the voltage sensor 260 and the loop antenna 270. Either the controller 250 or the voltage sensor 260 may also be configured with a memory. The controller 250 is electrically connected to the loop antenna 270 by interconnects 257 also situated on the substrate 230. Similarly, the controller 250 is electrically connected to the voltage sensor 260 by an interconnect 251. The interconnects 251, 257, the loop antenna 270, and any conductive electrodes (e.g., for a voltage sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the EMD 210, voltage sensor 260 is mounted to a side of the substrate 230 facing the convex surface 224. In some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the loop antenna can have a cutout to allow room for the controller 250 and voltage sensor 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and voltage sensor 260. Interconnects between the ends of such a wound antenna (e.g., the antenna leads) can then be passed through the substrate 230 to the controller 250.

Figure 2D:
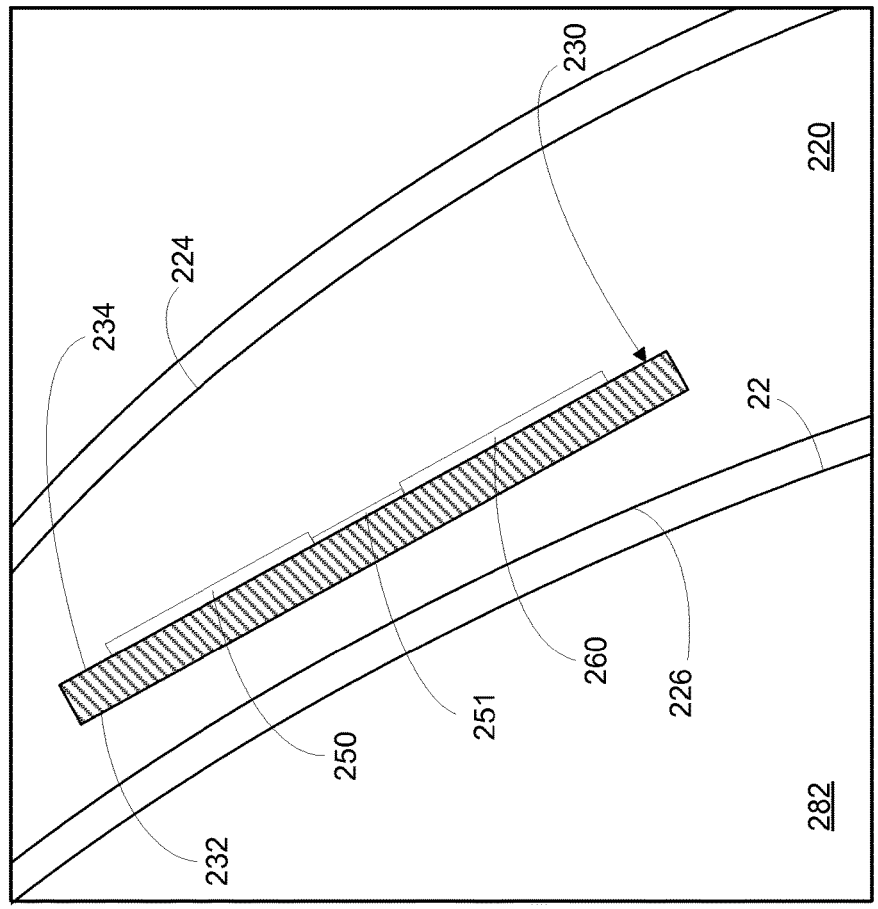
FIG. 2D is a side cross-section view of the example eye-mountable device when mounted as shown in FIG. 2C, in accordance with an example embodiment.
Figure 2C:
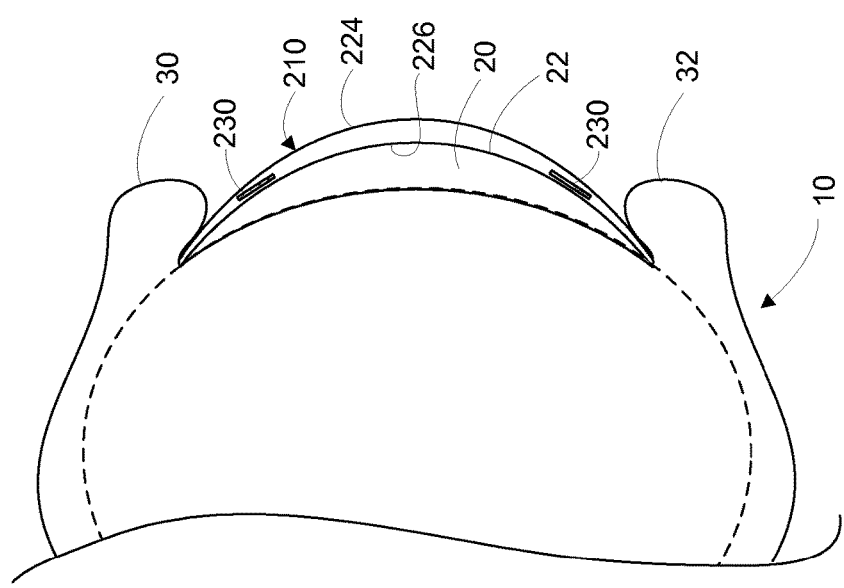
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the EMD 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the EMD 210 is mounted in the eye 10, a tear film coats both the concave and convex surfaces 224, 226 with an inner layer (along the concave surface 226) and an outer layer (along the convex layer 224). The tear film layers can be about 10 micrometers in thickness and together account for about 10 microliters.

The tear film layers are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the EMD 210. The tear film layer on the corneal surface 22 also facilitates mounting the EMD 210 by capillary forces between the concave surface 226 and the corneal surface 22. In some embodiments, the EMD 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the voltage sensor 260, controller 250, and conductive interconnect 251 may be mounted on the outward-facing surface 234. However, in other embodiments, the various components may also be mounted on the inward-facing surface.

The polymer layer defining the anterior side may be greater than 50 micrometers thick, whereas the polymer layer defining the posterior side may be less than 150 micrometers. Thus, voltage sensor 260 may be at least 50 micrometers away from the convex surface 224 and may be a greater distance away from the concave surface 226. However, in other examples, the voltage sensor 260 may be mounted on the inward-facing surface 232 of the substrate 230 such that the voltage sensor 260 are facing concave surface 226. The voltage sensor 260 could also be positioned closer to the concave surface 226 than the convex surface 224.

Figure 3:
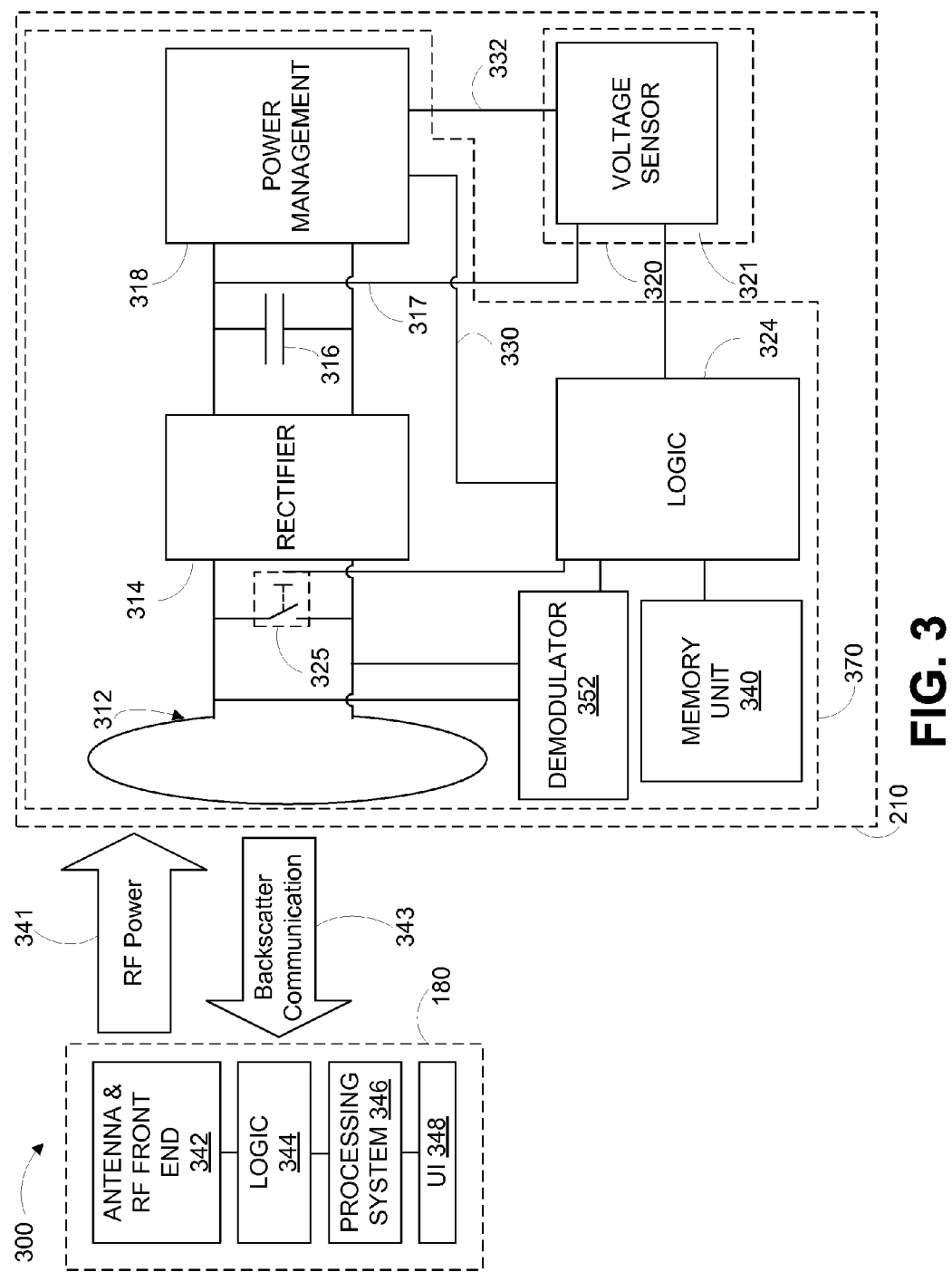
FIG. 3 is a functional block diagram of an example system for zero-power wireless device programming, in accordance with an example embodiment.

FIG. 3 is a functional block diagram of a system 300 for zero-power wireless device programming. The system 300 includes an EMD 210 (which may be an eye-mountable device) with embedded electronic components in communication with and powered by reader 180. Reader 180 and EMD 210 can communicate according to one communication protocol or standard, shown in FIG. 3 as RF Power 341. In one particular embodiment, the protocol used for RF Power 341 and backscatter communication 343 is an RFID protocol. The EMD 210 includes an antenna 312 for capturing radio frequency (RF) power 341 from the reader 180. In various embodiments, the RF power 341 from the reader 180 may have two components, a power component and a data component. The rectifier 314 may rectify the RF power into a supply voltage. The demodulator 352 may demodulate a portion of the RF power into a data stream. The antenna 312 may also create backscatter communication 343. Reader 180 can also be configured to communicate with a display device (the display device could be integrated with the reader 180 as UI 348).

The EMD 210 includes rectifier 314, energy storage 316 (that may output unregulated voltage 317), and power management 318 for generating regulated supply voltages 330, 332 to operate the embedded electronics. The EMD 210 includes a voltage sensor 321 that may have a sensor interface 320. The EMD 210 includes a processing unit, such as hardware logic 324, for communicating data, including results from the sensor 321 to the reader 180 by modulating the impedance of the antenna 312. The hardware logic 324 can also receive data communicated from reader 180. The demodulator 352 may demodulate the received data before being received by the logic 324. An impedance modulator 325 (shown symbolically as a switch in FIG. 3) can be used to modulate the antenna impedance according to instructions from the hardware logic 324. Similar to the eye-mountable device 110 discussed above in connection with FIG. 1, the EMD 210 can include a mounting substrate embedded within a polymeric material configured to be mounted to an eye.

Additionally, the logic 324 may be coupled to a memory unit 340. The logic 324 may be configured to store data to the memory unit 340. Also, the logic 324 may be configured to execute program instructions stored in the memory unit 340. Additionally, the memory unit 340 may include volatile memory, non-volatile memory, or both. For example, the memory 340 may be configured to store program instructions in volatile memory. If the energy storage 316 falls below a threshold voltage, volatile memory may lose the contents of its memory. However, the memory 340 may also be configured to store an cryptographic key in a non-volatile memory. The cryptographic key may be stored permanently. The cryptographic key may enable the logic to encrypt or decrypt data (such as program instructions or other data) and/or verify a digital signature of received data.

In some additional embodiments, the demodulator 352 may be connected directly to the memory unit 340. In embodiments where the demodulator 352 is connected directly to the memory unit 340, once received data is demodulated it may be directly written to the memory unit 340. When the memory is directly written to, the logic 324 may be configured to verify the data written to the memory unit 340 based on the cryptographic key.

With reference to FIG. 3, in various embodiments, the voltage sensor 321 measures either the unregulated voltage 317 or the regulated supply voltage 332. In various embodiments, the voltage measured by the voltage sensor 321 may come from different sources. As shown in FIG. 3, the power management 318 may provide the regulated supply voltage 332 and the energy storage 316 may provide unregulated voltage 317. However, in other embodiments, only one of the regulated supply voltage 332 and the unregulated voltage 317 may be provided to the voltage sensor 321. In additional embodiments, the regulated supply voltage 332 provided to the voltage sensor 321 may be the same regulated supply voltage 330 that supplies power to the hardware logic 324. The connections shown in FIG. 3 are one example of possible configurations for the voltage sensor 321. The sensor interface 320 may be configured as a part of the voltage sensor 321 itself. For example, the sensor interface 320 may convert the output of the voltage sensor 321 into a format that in understandable by the hardware logic 324.

In other embodiments, the sensor interface 320 can contain an electrical sensor other than voltage sensor 321. For example, a current sensor, a power sensor, or other electrical sensor may be used in the place of the voltage sensor 321 within the context of the present disclosure. The connections to the sensor interface 320 may change depending on the specific type of sensor that forms a portion of sensor interface 320. For example, the sensor unit 320 contains a parallel electrical connection to the hardware logic 324. A current sensor may be placed in a series electrical connection with one of the hardware logic 324, voltage power management 318, or other component. Additionally, the sensor interface 320 may contain other sensors, such a glucose sensor.

The rectifier 314, energy storage 316, and power management 318 operate to harvest energy from received RF power 341. RF power 341 causes radio frequency electrical signals on leads of the antenna 312. The rectifier 314 is connected to the antenna leads and converts the radio frequency electrical signals to a DC voltage. The energy storage 316 (e.g., capacitor or battery) is connected across the output of the rectifier 314 to filter out high frequency components of the DC voltage. The power management 318 receives the filtered DC voltage (e.g unregulated voltage 317) and outputs both a regulated supply voltage 330 to operate the hardware logic 324 and a regulated supply voltage 332 to operate the voltage sensor 321 of the sensor interface 320. For example, the supply voltage can be equivalent to the voltage of the energy storage 316. In another example, the supply voltage can be equivalent to the voltage of the rectified DC voltage from the rectifier 314. Additionally, the regulated supply voltage 330 can be a voltage suitable for driving digital logic circuitry and memory circuitry, such as approximately 1.2 Volts, approximately 3 Volts, etc. The voltage needed as the regulated supply voltage 330 may change depending on a functionality requirement of the logic 324 (or a voltage requirement of other components of the EMD 210). Reception of the RF power 341 from the reader 180 (or another source, such as ambient radiation, etc.) causes the regulated supply voltages 330, 332 to be supplied to the sensor 320 and hardware logic 324. While powered, the sensor 320 and hardware logic 324 are configured to generate and measure a voltage (such as either unregulated voltage 317 or regulated supply voltages 332) and communicate the results.

The sensor results can be communicated back to the reader 180 via backscatter radiation 343 from the antenna 312. The hardware logic 324 receives the supply voltage from the sensor interface 320 (or the voltage sensor 321 itself) and modulates (325) the impedance of the antenna 312 in accordance with the supply voltage measured by the sensor 320. The antenna impedance and/or change in antenna impedance are detected by the reader 180 via the backscatter signal 343.

Reader 180 can include an antenna and RF front end 342 and logic components 344 to communicate using a radio protocol, decode the information indicated by the backscatter signal 343, provide digital inputs to a processing system 346 and receive inputs and/or provide outputs via user interface (UI) 348. The radio protocol can be, for example, an RFID protocol. In some embodiments, part or all of EMD 210 can be configured to perform some or all features of an RFID tag. For example, as shown in FIG. 3, some or all of the components shown as tag 370 of EMD 210 can perform some or all features of an RFID tag; e.g., antenna 312, rectifier 314, energy storage 316, voltage power management 318, hardware logic 324, etc.

In some embodiments, one or more of the features shown as separate functional blocks can be implemented ("packaged") on a single chip. For example, the EMD 210 can be implemented with the rectifier 314, energy storage 316, power management 318, sensor interface 320, memory unit 340 and the hardware logic 324 packaged together in a single chip or controller module. Such a controller can have interconnects ("leads") connected to the loop antenna 312 and the sensor electrodes. Such a controller operates to harvest energy received at the loop antenna 312, measure the supply voltage created by the harvested energy, and indicate the measured supply voltage via the antenna 312 (e.g., through the backscatter communication 343).

A processing system, such as, but not limited to, processing system 346, can include one or more processors and one or more storage components. Example processor(s) include, but are not limited to, CPUs, Graphics Processing Units (GPUs), digital signal processors (DSPs), application specific integrated circuits (ASICs). Example storage component(s) include, but are not limited to volatile and/or non-volatile storage components, e.g., optical, magnetic, organic or other memory, disc storage; Random Access Memory (RAM), Read-Only Memory (ROM), flash memory, optical memory unit, and disc memory. The storage component(s) can be configured to store software and data; e.g., computer-readable instructions configured, when executed by a processor of the processing system, to cause the processing system to carry out functions such as but not limited to the herein-described functions of reader 180, EMD 210, and/or display device 350.

The reader 180 can associate the backscatter signal 343 with the sensor result (e.g., via the processing system 346 according to a pre-programmed relationship associating impedance of the antenna 312 with output from the sensor 320). The processing system 346 can then store the indicated sensor results (e.g., induced supply voltage) in a local memory and/or an external memory (e.g., by communicating with the external memory either on display device 350 or through a network). The processing system 346 may be configured to communicate program instructions from the reader 180 to the EMD 210 when the sensor indicates a voltage is high enough for volatile memory to be written to. For example, the processing system 346 may determine when the voltage induced in the EMD 210 is higher than the memory unit 340 voltage threshold and responsively communicate program instructions to the EMD 210.

The tag may be able to measure and record the level of the rectified voltage that the reader can access by reading a register via the RFID communication protocol. Block 321 in FIG. 3 illustrates this capability. The voltage sensor value is converted to digital via an analog-to-digital converter (ADC) and stored in a register that is addressable by the reader.

In some embodiments, the processing system 346 of the reader 180 may alter how much power is transmitted to the EMD 210 from the reader 180 based on the calculated proximity and/or link quality. For example, if the reader 180 determines that an alignment is off or the link quality is low, the reader 180 may increase the power transmitted to the EMD 210. However, if the reader 180 determines that an alignment is good or the link quality is high, the reader 180 may decrease the power transmitted to the EMD 210.

As previously discussed, the logic 324 may be coupled to a memory unit 340 and the logic 324 may be configured to store data to the memory unit 340. In various embodiments, the memory unit 340 may include volatile memory, non-volatile memory, or both volatile memory and non-volatile memory.

A volatile memory is a memory that generally requires electrical power to retain data. When electrical power to a volatile memory falls below a threshold power level, the data in the memory may be lost or corrupted. The data may be lost or corrupted as soon as the power falls below the threshold, or after a period of time after the power falls below the threshold. Volatile memory may have some advantages over non-volatile memory. For example, volatile memory may operate at a higher speed than non-volatile memory. Volatile memory may use less electrical power for read and write operations than non-volatile memory. Additionally, volatile memory may be created smaller than non-volatile memory and may also be less expensive to manufacture. Further, because volatile memory loses data when the power supplied to the memory falls below a threshold level, the data stored in a volatile memory may be more secure than data stored in a non-volatile memory.

Conversely, a non-volatile memory retains data even when no power is supplied to the memory. Thus, in situations where data retention is critical, a non-volatile memory may be preferable. Additionally, some forms of non-volatile memory may only allow data to be written to the memory one time. Non-volatile memory that only allows a single write operation may be known as Read Only Memory (ROM).

In some embodiments, the memory unit 340 of the EMD 210 may include both a volatile component and a non-volatile component. For example, the non-volatile component may be configured to store a secure cryptographic key. The non-volatile component may be a ROM. In some embodiments, a secure cryptographic key may be stored to the ROM when an EMD 210 is programmed in a factory. In other embodiments, the secure cryptographic key may be programmed by a device vendor, or even by an end user. The secure cryptographic key may be used by the logic 324 to decrypt received data or encrypt data for communication. Additionally, the cryptographic key may be used to verify the authenticity of data received by the EMD 210. In some embodiments, if the key is re-programmable (e.g. stored in volatile memory or multi-time programmable non-volatile memory), the tag may delete stored information when a new cryptographic key is issued to restrict data access to the new key issuer. Additionally, if the key has already been programmed, the tag may restrict access to re-programming a new key until a command has been issued to release the first key. Issuance of this "release" command by a reader may be encrypted or authenticated using the original key. In this way, the EMD may be paired with a single user's reader(s) until the user or system chooses to un-pair.

The memory 340 may be configured to store program instructions in volatile memory of the memory unit 340. However, because if the energy storage 316 falls below a threshold voltage volatile memory may lose the contents of its memory, it may be desirable to store program instructions in the memory at a time when the EMD 210 may routinely be charged. When an EMD 210 is built in a factory, the charge in energy storage 316 may not supply enough power to the memory unit 340 for factory-programmed program instructions to still be stored in the volatile memory unit when the EMD 210 is put into use. Thus, a period of time after an EMD 210 leaves the factory the volatile memory may lose all stored information. Thus, in some embodiments, an EMD 210 may undergo an initialization process to both have energy storage 316 charged and program instructions stored to memory 340 before operation. Before program instructions are stored to memory unit 340, the EMD 210 may communicate a voltage level from the EMD 210 to the reader 180. In some other embodiments, other measure of accumulated charge level (such as integration of current), or measure of current flowing into battery (which indicates that the constant-voltage charging stage is complete when current falls below a threshold) may be communicated from the EMD 210 to the reader 180 before program instructions are communicated. The reader 180 may communicate program instructions to be stored to memory 340 once the voltage level induced in the EMD 210 are greater than a threshold to enable functionality of the volatile memory of the memory unit 340

In some embodiments, reader 180 can communicate with devices in addition to EMD 210 or tag 370. For example, the reader 180 may also function as a cellular phone or other wireless communication device.

Figure 4:
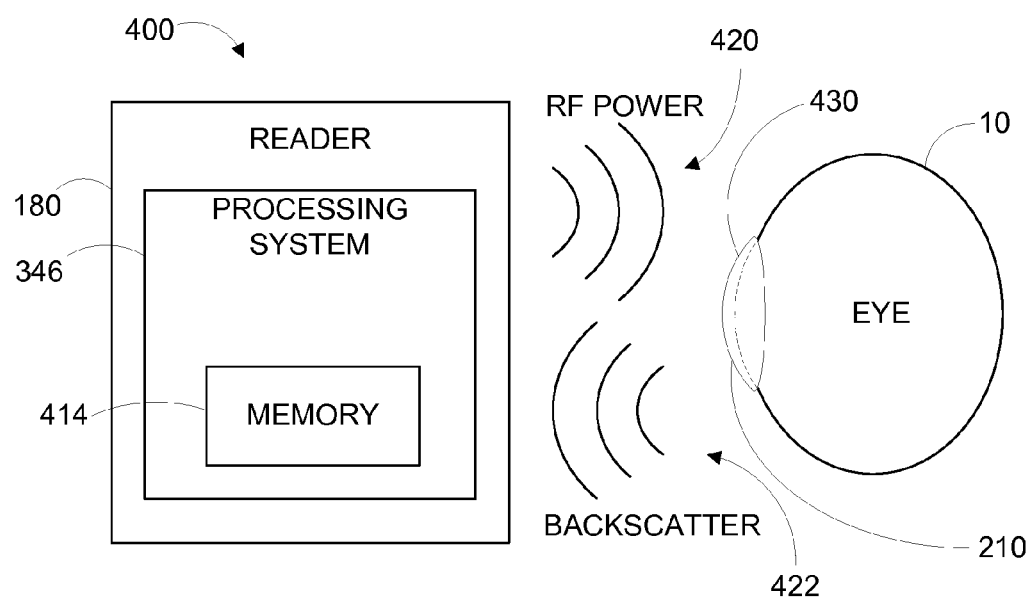
FIG. 4 is a block diagram of an electrical sensor system operated by a reader for zero-power wireless device programming, in accordance with an example embodiment.

FIG. 4 is a block diagram of a system 400 with EMD 210 operated by a reader 180 to obtain a series of supply voltage measurements over time. An electrical sensor; e.g., an embodiment of sensor 321, can be included with EMD 210. As shown in FIG. 4, EMD 210 is configured to be contact-mounted over a corneal surface of an eye 10. The ophthalmic electrical sensor can be operated to be transitioned into an active measurement mode in response to receiving a signal from the reader 180.

The reader 180 includes a processing system 346, configured with memory 414. The processing system 412 can be a computing system that executes computer-readable instruction stored in the memory 414 to cause the reader 180/system 400 to obtain a time series of measurements by intermittently transmitting a measurement signal to EMD 210. In response to the measurement signal, one or more sensors of EMD 210; e.g., electrical sensor 430, can take measurement(s), obtain results of the measurement(s), and communicate the results to reader 180 via backscatter 422. As discussed above regarding FIG. 3, reader 180 can provide RF power, such as RF power 420, to be harvested by the EMD 210. For example, impedance of an antenna of EMD 210 can be modulated in accordance with the sensor result such that the backscatter radiation 422 indicates the sensor results. Reader 180 can also use memory 414 to store indications of supply voltage measurements communicated by the voltage sensor 430. The reader 180 can thus be operated to intermittently power the electrical sensor 430 so as to obtain a time series of supply voltage measurements.

A wearer of eye-mountable devices may also wear a reader device as well. The reader devices may be configure as part of various other items such as a band, earrings, and a necklace, to name a few possibilities. The functionality of a reader in a band can be performed by a structure of another device, e.g., an eye-glass frame, a head-mountable computer frame, a cap, a hat, part of a hat or cap (e.g., a hat band or bill of a baseball cap), a headphone headband, etc., or by a separate band; e.g., a head band, a scarf or bandanna worn as a head band. For examples, ear(s), nose, hair, skin, and/or a head of wearer can support a reader band, and perhaps by external devices e.g., stick pins, bobby pins, headband elastics, snaps. Other and different support(s) for a reader band are possible as well.

One or more of band, earrings, and necklace can be configured to include one or more readers; e.g., the above-mentioned reader 180. For example, readers can be placed in one or more various locations near the tags. To power and communicate with a sensor in an eye-mounted tag, a reader, such as reader 180, can be mounted on the face of a wearer of the eye-mounted tags, such being formed into eyeglasses. Additionally, readers may be configured to be located in earrings, a necklace, etc. Other embodiments are possible as well; e.g., readers can be configured as part of a hat, headband, scarf, jewelry (e.g., a brooch), glasses, HMD, and/or other apparatus.

In some embodiments, a reader can power a sensor in EMD 210 using a low-power transmission; e.g., a transmission of 1 watt or less of power. In these embodiments, the reader can be within a predetermined distance; e.g., 1 foot, 40 cm, of the tag to power the sensor.

Figure 5:
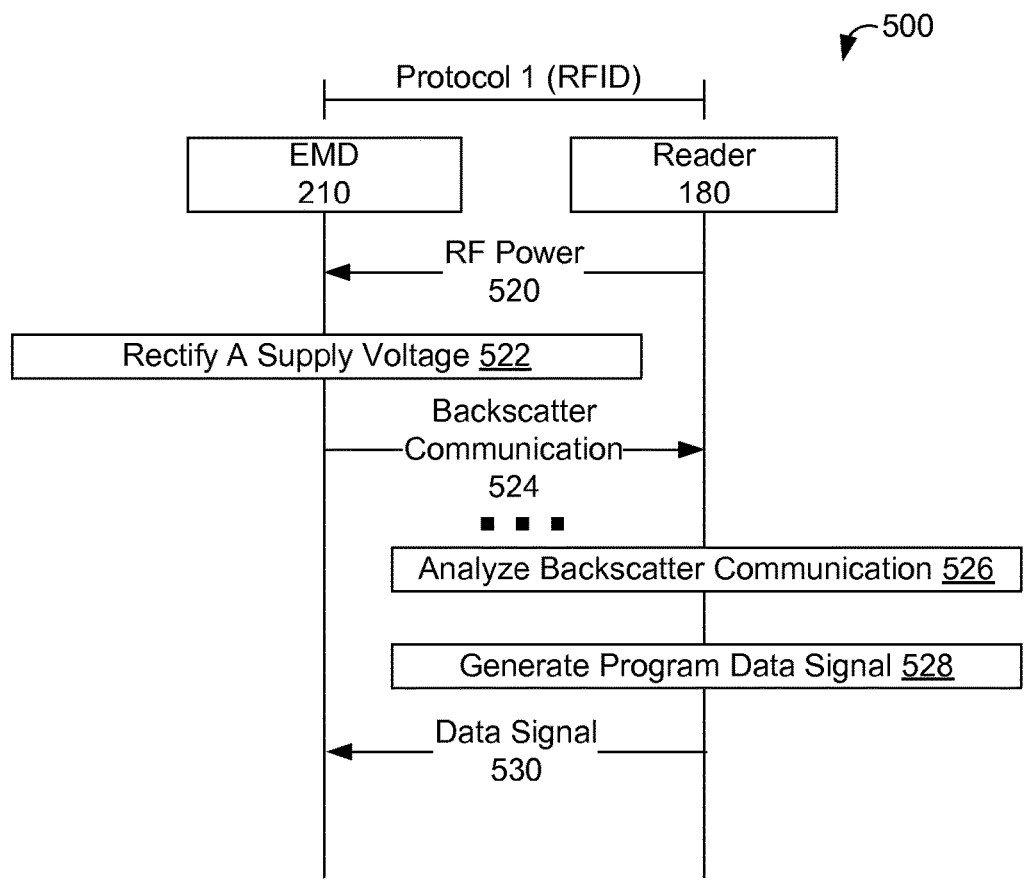
FIG. 5 shows a scenario where a reader communicates with an eye-mountable device and a handheld device, in accordance with an example embodiment.

FIG. 5 shows a scenario 500 where reader 180 communicates with an eye-mountable device (EMD) 210. In scenario 500, EMD 210 and reader 180 communicate using an RFID protocol; e.g., an RFID Generation 2 protocol such as specified in "EPC™ Radio-Frequency Identity Protocols Class-1 Generation-2 UHF RFID Protocol for Communications at 860 MHz-960 MHz, Version 1.2.0", Oct. 23, 2008, EPCglobal Inc.

In other scenarios, the reader, tag, display device, and/or other device(s) can communicate using different and/or additional protocols; e.g., an IEEE 802.11 protocol ("Wi-Fi"), an IEEE 802.15 protocol ("Zigbee"), a Local Area Network (LAN) protocol, a Wireless Wide Area Network (WWAN) protocol such as but not limited to a 2G protocol (e.g., CDMA, TDMA, GSM), a 3G protocol (e.g., CDMA-2000, UMTS), a 4G protocol (e.g., LTE, WiMAX), a wired protocol (e.g., USB, a wired IEEE 802 protocol, RS-232, DTMF, dial pulse). Many other examples of protocol(s) and combination(s) of protocols can be used as well. For example, some technologies, such as RFID, may include encryption technologies in future revisions. These encrypted wireless protocols may be used within the context of the present disclosure.

Although scenario 500 in shown in a linear order, the blocks may also be performed in a different order. Additionally, in some embodiments, at least one block of scenario 500 may be performed in parallel to another block of scenario 500.

Scenario 500 begins with reader 180 sending a communication to the EMD 210 of an eye-mountable device (EMD) with a transmit RF Power 520. The transmitted RF Power 520 may be a radio signal with a defined radio power. In some embodiments, the radio power may be transmitted as a continuous wave (CW) radio signal or the radio power may be transmitted as a pulse-modulated radio signal. In other embodiments, the RF Power 520 transmission may take a form other than a CW or pulse-modulated radio signal. In some embodiments, the communication may be an initialization of the EMD 210. However, in other embodiments, the communication may be the normal operation of the EMD 210.

When the EMD 210 receives the RF power 520, it rectifies a supply voltage 522 from the RF power 520. The supply voltage is used to power various components within the EMD 210. The EMD 210 may also be configured to measure the supply voltage created in the EMD 210. The EMD 210 may include an electrical component configured to measure the supply voltage induced in the EMD 210 from the RF power 520. Additionally, the EMD 210 may be configured to create a backscatter signal based on the supply voltage. In some embodiments, the EMD 210 may also measure a voltage (or other electrical characteristic) of the rectified supply voltage. The EMD 210 may communicate the measured voltage (or other electrical characteristic) via the backscatter signal.

After transmitting RF Power 520 to an EMD 210, the reader 180 may responsively receive a backscatter communication 524 communicated from the EMD 210. The EMD 210 may communicate the backscatter communication 524 through backscatter radiation of the RF Power 520. The backscatter radiation may be created by a modulation of an impedance of an antenna of the EMD 210. The EMD 210 may be configured to modulate the antenna impedance to create a signal to communicate a supply voltage induced in the EMD 210 by RF Power 520.

Once the reader 180 receives the backscatter communication 524, it may analyze the backscatter communication 526. When the reader 180 analyzes the backscatter communication 526, it may determine a voltage induced in the EMD 210 by the RF Power 520 from the reader 180 the reader 180. In some embodiments, analyzing the backscatter communication 526 may determine that a signal received as backscatter communication 524 contains an indication of the supply voltage in the EMD 210. As previously discussed, the reader 180 may use the measured supply voltage to determine if the supply voltage is high enough to power a memory unit of the EMD 210.

In some embodiments, the EMD 210 may not measure (or communicate) the supply voltage to the reader 180. In this instance, the lack of an indication of a supply voltage may indicate to the reader 180 that the reader may use parameters of the backscatter communication 524 to calculate the supply voltage in the EMD 210. The parameters that may be calculated for the backscatter communication 524 may be, but are not limited to, a received power level of the backscatter communication 524, a power ratio of the backscatter communication 524 and the RF Power 520, a bit error rate of the backscatter communication 524, a data rate of the backscatter communication 524, the existence of backscatter communication 524, and/or other parameters of the backscatter communication 524. As previously discussed, the reader 180 may use the parameters of the backscatter communication 524 to determine if the supply voltage is high enough to power a memory unit of the EMD 210.

Once the reader 180 analyzes the backscatter communication 524, it may responsively generate program data signal 528. The program data signal 528 of the reader 180 may include encoded program instructions as data for transmission to the EMD 210. Additionally, reader 180 may encode the program instruction in a way the EMD 210 may be able to verify the authenticity of the program instructions. For example, program instructions that may operate the EMD 210 may be encoded based on a secure cryptographic key to form program data signal 528.

Once the reader 180 generates program data signal 528, the program data signal 528 may be communicated to the EMD 210 via data signal 530. Data signal 530 may be transmitted either simultaneously or separate from RF Power 520. For example, the transmitted RF Power 520 may be a radio signal with a defined radio power and also contain modulated data corresponding to data signal 530. In some embodiments, the combination of the RF Power 520 and the data signal 530 may be transmitted as a continuous wave (CW) radio signal or the radio power may be transmitted as a pulse-modulated radio signal. In other embodiments, the RF Power 520 and data signal 530 any transmissions may take a form other than a CW or pulse-modulated radio signal.

Figure 6:
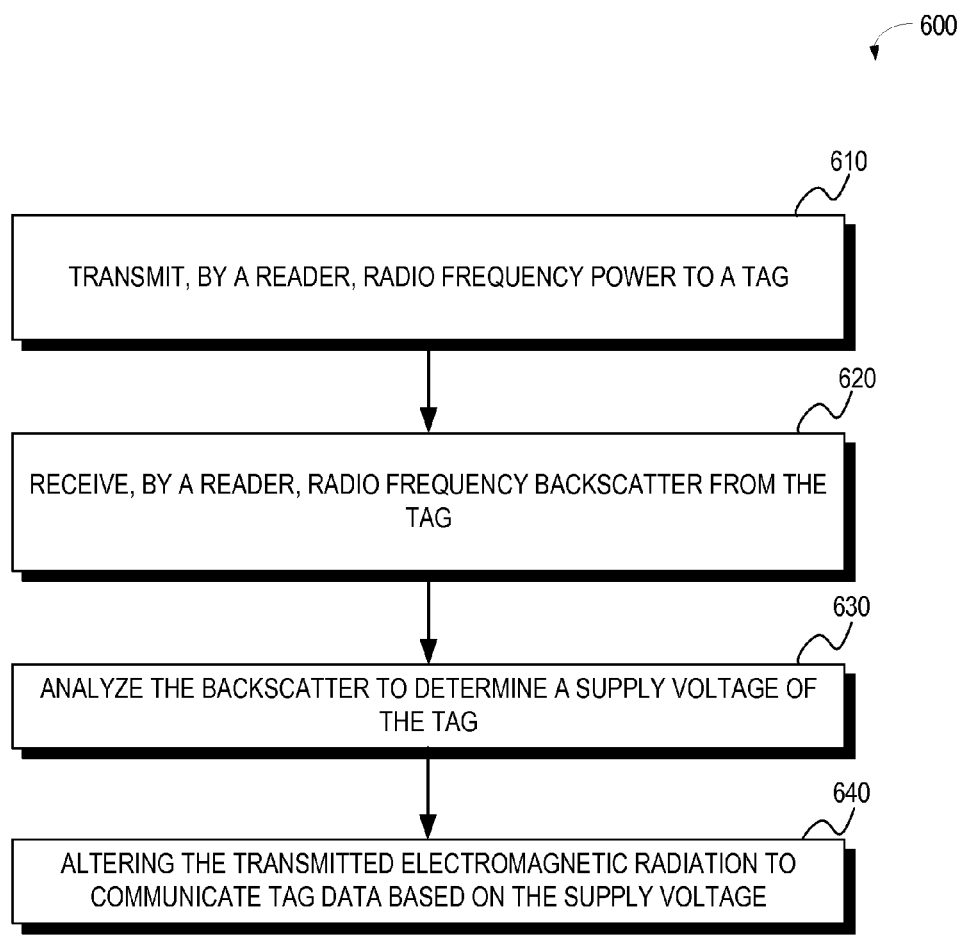
FIG. 6 is a flow chart of an example method, in accordance with an example embodiment.

FIG. 6 is a flow chart of an example method 600. Method 600 can be carried out by a device, such as a tag in an body-mountable device, or a device that includes a processor, such the hardware logic 324, the hardware logic may include a computer readable medium storing machine-readable instructions, such as the memory unit 340, where the machine-readable instructions, when executed by a processing component of the device, are configured to cause the device to carry out some or all of the techniques described herein as method 600.

Method 600 can begin at block 610. At block 610, the tag can receive RF power, such as discussed above in the context of at least FIG. 5. An antenna in the tag may receive the RF power and output a supply signal. The supply signal may be proportional to the received RF signal. The tag can be part of an body-mountable device; e.g., tag 370 of EMD 210, such as discussed above in more detail in the context of at least FIG. 3. In some embodiments, the reader can be within a predetermined distance from the tag when transmitting RF power to the tag, such as discussed above. In other embodiments, the reader can be part of an HMD, such as discussed above.

At block 620, the reader receives a radio frequency backscatter from the tag. The tag may create the backscatter. To create backscatter, the tag may vary an impedance of an antenna in the tag. In some embodiments, the backscatter may contain data. The data may include an acknowledgement signal indicating the tag is functional. The data may also include a status of a memory unit of the tag. For example, the data may indicate whether or not the memory unit contains program instructions. In additional embodiments, the data may contain a signal indicating the voltage induced in the tag by the RF power transmitted to the tag at block 610.

At block 630, once the reader receives the backscatter from the tag, it may analyze the backscatter communication to determine a supply voltage that has been induced in the tag. The reader may also determine a memory programming state of the tage. When the reader analyzes the backscatter communication, it may determine if the supply voltage is of a sufficient level for a volatile memory to be in an operational mode.

At block 640, the reader may alter the transmitted electromagnetic radiation to communicate data based on the supply voltage. The communicated data may take the form of program instructions. In some embodiments, when the supply voltage is of a sufficient level for a volatile memory to be in an operational mode, the reader may responsively communicate program instructions from the reader to the tag for the tag to store in a volatile memory. Additionally, the reader may be configured to only communicate program instructions to the tag when the tag indicated it currently has no stored program instructions. As previously discussed, the reader may also encrypt the program instructions before communicating them to the tag.

When the tag receives data, it may perform various functions based on the embodiment. In some embodiments, the tag may directly store received program instructions in a memory unit of the tag. In other embodiments, a processing unit of the tag, such as the logic 324, may verify the program instructions before they are stored to the memory unit. The program instructions may be verified based on a cryptographic key. The cryptographic key may be used to either decrypt the received program instructions or verify a signature of the program instructions before they are stored in memory.

In embodiments where the tag directly stores the program instruction to the memory, once program instructions are stored in the memory they may either be decrypted by a processing unit of the tag or executed by a processing unit of the tag. If the program instructions are transmitted in an encrypted manner, they may need to be decrypted before they can be executed. The decryption may be performed based on a stored cryptographic key. By decrypting the program instructions, the program instructions are both converted into a form that can be executed, as well as the program instructions are verified to have been encrypted with a valid cryptographic key. Additionally, as previously discussed, a signature of the program instructions may also be verified based on the cryptographic key. Verifying the program data was encrypted may prevent unauthorized program instructions from being stored to the tag.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or nonvolatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A reader apparatus comprising:
an antenna configured to:
    transmit electromagnetic radiation, and
    receive backscatter electromagnetic radiation; and
a processing unit configured to:
    analyze the backscatter electromagnetic radiation to determine both a supply voltage and that a tag has no stored program instructions in a volatile memory: and
in response to both the supply voltage being greater than a threshold voltage required to power the volatile memory of the tag and determining the tag has no stored program instructions in the volatile memory, communicate program instructions for storage in the volatile memory and for execution by the tag from the volatile memory and a nonvolatile memory configured to store a cryptographic key.

2. The reader apparatus according to claim 1, wherein the processing unit is further configured to encrypt the tag data.

3. The reader apparatus according to claim 1, wherein the backscatter radiation comprises a data stream.

4. The reader apparatus according to claim 3, wherein the processing unit is further configured to decrypt the data stream.

5. The reader apparatus according to claim 3, wherein the processing unit is configured to verify a correct data write based on the data stream.

6. The reader apparatus according to claim 1, wherein the transmitted electromagnetic radiation is configured to provide power.

7. A body-mountable device comprising:
A volatile memory of the body-mountable device;
a nonvolatile memory configured to store a cryptograpic key;
an antenna of the body-mountable device configured to:
    receive first electromagnetic radiation during a first period of time,
    receive second electromagnetic radiation during a second period of time, wherein the received second electromagnetic radiation communicates program instructions, and
    output a first signal indicative of both a supply voltage being greater than a threshold voltage required to power the volatile memory of the body-mountable device based on the received first electromagnetic radiation and an indication that the body-mountable device currently has no stored program instructions in the volatile memory;
a rectification circuit of the body-mountable device configured to rectify at least the first signal to generate the supply voltage;
wherein the volatile memory is powered by the supply voltage and configured to store the program instructions communicated via the second electromagnetic radiation; and a processing unit of the body-mountable device configured to execute the program instructions stored in the volatile memory.

8. The body-mountable device according to claim 7, further comprising:
the processing unit is further configured to authenticate the data communicated via the electromagnetic radiation.

9. The body-mountable device according to claim 8, wherein the antenna, rectification circuit, volatile memory, nonvolatile memory, and processing unit are contained within a contact lens.

10. The body-mountable device according to claim 8, where the processing unit is further configured to decrypt the data.

11. The body-mountable device according to claim 7, wherein the rectification circuit is further configured to rectify at least a portion of the second signal to generate the supply voltage.

12. The body-mountable device according to claim 11, wherein the rectification circuit is further configured to charge an energy storage device.

13. A method comprising:
transmitting electromagnetic radiation,
receiving backseatter electromagnetic radiation;
analyzing the backscatter electromagnetic radiation to determine both a supply voltage and that a tag has no stored program instructions in a volatile memory; and
in response to both the supply voltage being greater than a threshold voltage required to power the volatile memory of the tag and determining the tag, has no stored program instructions in the volatile memory, communicating program instructions for storage in the volatile memory and for execution by the tag from the volatile memory and a nonvolatile memory configured to store a cryptographic key.

14. The method according to claim 13, further comprising encrypting the tag data.

15. The method according to claim 13, wherein the backscatter radiation comprises a data stream.

16. The method according to claim 15, further comprising decrypting the data stream.

17. The method according to claim 15, further comprising verifying a correct data write based on the data stream.

18. The method according to claim 13, wherein the transmitted electromagnetic radiation is configured to provide power.

* * * * *